(12) United States Patent
Jamir et al.

(10) Patent No.: US 6,528,265 B2
(45) Date of Patent: Mar. 4, 2003

(54) DNA MARKERS FOR ASSESSING SEED PURITY AND METHOD OF USING DNA SEQUENCES FOR ASSESSING SEED PURITY

(75) Inventors: Yashitola Jamir, Hyderabad (IN); Ramesh V. Sonti, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/820,182

(22) Filed: Mar. 28, 2001

(65) Prior Publication Data

US 2003/0027138 A1 Feb. 6, 2003

(51) Int. Cl.$^7$ .......................... C12Q 1/68; C12P 19/34; C07H 21/02; C07H 21/04
(52) U.S. Cl. .................. 435/6; 435/91.2; 536/23.1; 536/29.3
(58) Field of Search .................. 435/6, 91.2; 536/23.1, 536/24.3

(56) References Cited

U.S. PATENT DOCUMENTS 6,066,779 A   5/2000   Yan

OTHER PUBLICATIONS

Genebank accession No. D21251.1, "Mitochondrion Oryza sativa genes for ribosomal protein S3, L16, S12 and NADH dehydrogenase subunit 3", Apr. 14, 2000.*
Temnykh et al., Mapping and genome organization of microsattelite sequences in rice (*Oryza sativa* L.), *Theor Appln Genet*, 100:697–712 (2000).
Mao et al., "Technological innovations to lower the cost of hybrid rice seed production," Advances in Hybrid Rice Technology. Proc. Third Intl. Symp. on Hybrid Rice, Directorate of Rice Research, Chapter 11, (1996).
Kochert et al., *RFLP Training Course Laboratory Manual*, Rockefeller Foundation (Jul. 1989).
Hossain, "Economic prosperity in Asia: implications for rice research," In Khush (ed) Rice Genetics III, Proc. Third Intl. Rice Genet. Symp., Los Banos Manila, the Philippines, pp. 3–16 (1996).
*Seed Tech News*, 26:2, pp. 1,2,4 (Jun. 1996).

Williams et al., "DNA polymorphisms amplified by arbitrary primers are useful as genetic markers," *Nucleic Acids Research*, 18:22, pp. 6531–6535 (1990).
Wu et al., "Abundance, polymorphism and genetic mapping of microsatellites in rice," *Mol Gen Genet*, 241:225–235 (1993).
McCouch et al., "Development of microsatellite markers and characterization of simple sequence length polymorphism in rice (*Oryza sativa* L.)," Rice Genetics III, Proc. Third Intl. Rice Genet. Symp. Los Banos Manila, the Philippines, pp. 549–559 (1996).
Robeniol et al., "Sequence–tagged sites and low–cost DNA markers for rice," In Khush, G. S. (ed) Rice genetics III. Proc. Third Intl. Rice Genet. Symp. Los Banos Manila, the Philippines, pp. 293–306 (1996).
Altschul et al., "Gapped BLAST and PSI–BLAST: a new generation of protein database search programs," *Nucleic Acids Research*, 25:17, pp. 3389–3402 (1997).
Virmani, "Hybrid Rice," *Advances in Agronomy*, 57:377–462 (1993).
Powell et al., "Polymorphism revealed by simple sequence repeats," 1:7, pp. 215–222 (Jul. 1996).
Ghareyazie et al., "Classification of rice germplasm. I. Analysis using ALP and PCR–based RFLP," *Theor Appl Genet*, 91:218–227 (1995).
Sambrook et al., *Analysis of Genomic DNA by Southern Hybridization*, 9.31–9.62 (1989).
Yuan, "Current status of hybrid rice in China and future strategies for 21st century," In Ahmed, M. I., and Viraktamath, B. C (eds) Hybrid rice seed production technology, Directorate of Rice Research, Hyderabad, India, p. 31–33 (1995).
Saleh et al., "Small mitochondrial DNA molecules of wild abortive cytoplasm in rice are not necessarily associated with CMS," *Theor Appl Genet*, 77:617–619 (1989).
Viraktamath et al., "Use of isozyme marker amp $3^2$ for identifying wide compatible varieties," *Hybrid Rice Newsletter* (1995).

* cited by examiner

Primary Examiner—Kenneth R. Horlick
Assistant Examiner—Teresa Strzelecka
(74) Attorney, Agent, or Firm—Merchant & Gould, P.C.

(57) ABSTRACT

The invention relates to DNA markers specific to WA cytoplasmic male sterile lines of rice, for assessing seed purity and a method for ensuring the purity of cytoplasmic male sterile lines of rice using the said DNA based markers.

12 Claims, 8 Drawing Sheets

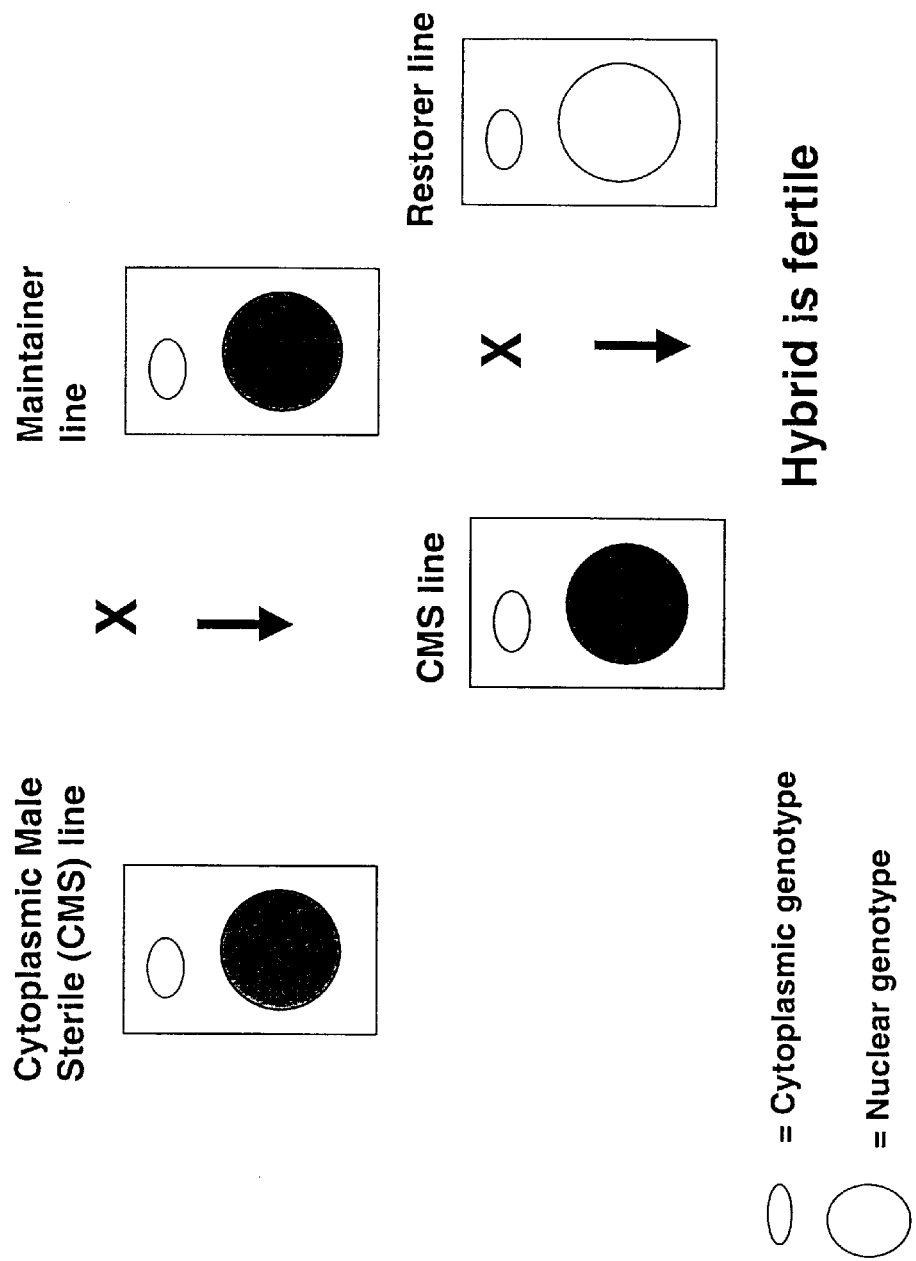
Figure 1. The three line system for hybrid rice production

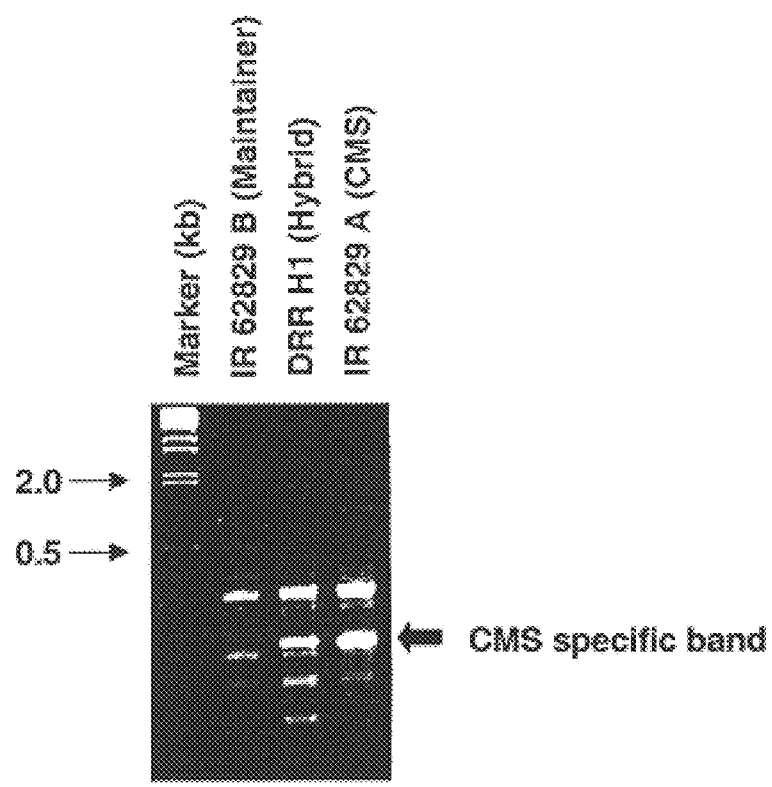
Figure 2. PCR amplification of a DNA sequence that is specific to CMS lines of rice Figure 3. Nucleotide sequence of a rice Cytoplasmic Male Sterile (CMS) line specific DNA (SEQ ID No. 1).

```
1    ACG GCC CTC ATC ACC TTC TTT CAC TTT TTG TTT TTG TGT AGG TGA GTC AAT TGC GTG TGG
61   CCT TCA AGT ATT TCG TAT TGT AAC AAT ATT CGA TCG GCA TCC AAA CAA AGG TGC ATG TAC
121  GGT TCC TAA GGG ATA CAA TTT TGT CTT AAA TCA TCG AGA AAG ATT AAG GTA AGT TGA TAG
181  GCG CGA TCT CGT ACC TAA CAC ATA CTC TCT AAA TAT TGA AGA ACT TGC ATG CGG CCT TCA
241  AGC CAC AAC GCG GTA TGA GTT CTT TGT TTG GGG GCT GCT TGC CCC TTC GCG TCG ACA AGG
301  AAA CTG AGG ACG ACA ATG GCA CC
```

Base positions 1 to 36 = A stretch of sequence which does not exhibit homology to the sequence of rice mitochondrial DNA, deposited as DBJ Accession # D21251.

Figure 4. Homology of Cytoplasmic Male Sterile (CMS) specific DNA sequence with rice mitochondrial DNA (SEQ ID No. 2).

CMS = Cytoplasmic Male Sterile specific sequence.

Mit = Part of the rice mitochondrial DNA, DBJ Accession # D21251.

Identical nucleotides are represented by the shaded area.

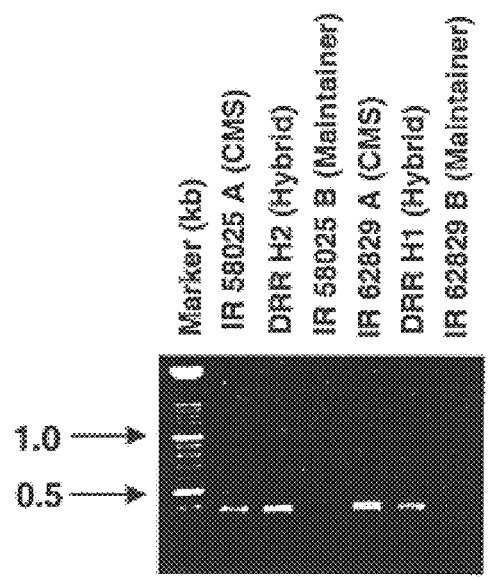
Figure 5. A PCR assay for distinguishing CMS and Maintainer lines of rice Figure 6. Detection of Restriction Fragment Length Polymorphism between CMS and Maintainer lines of rice using CMS specific DNA sequence as a probe
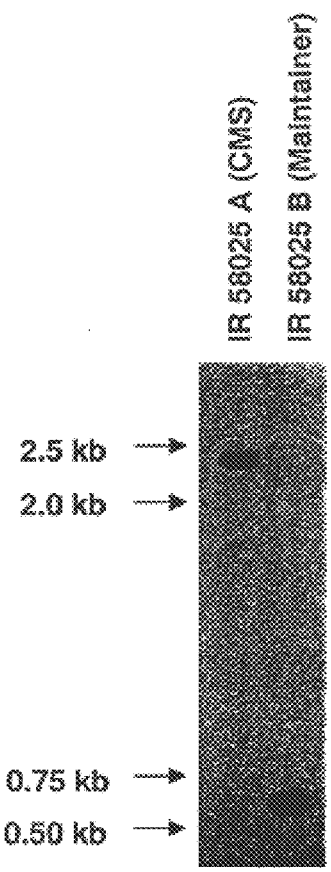

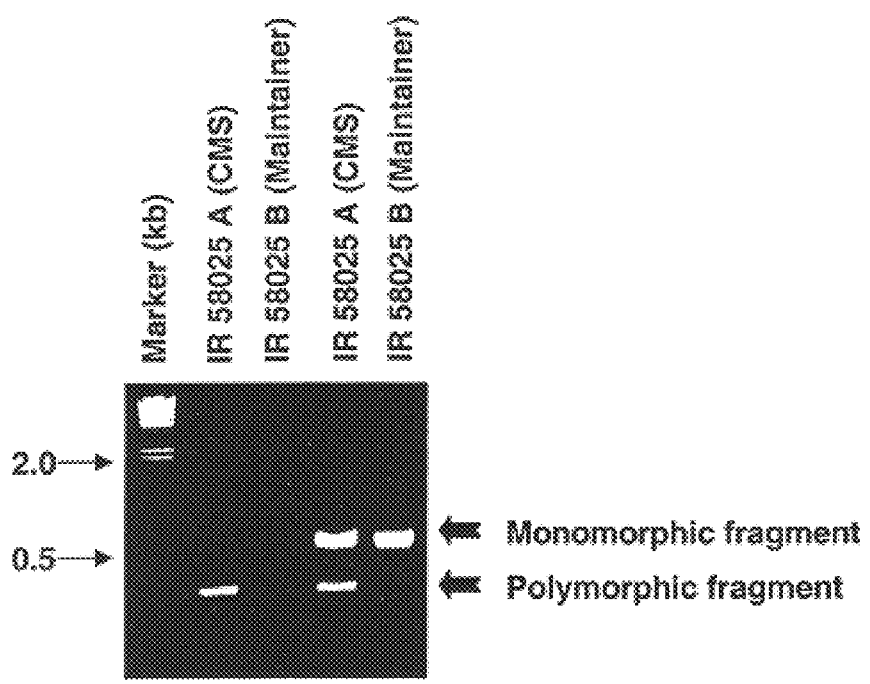
Figure 7. A multiplex PCR assay for distinguishing CMS and Maintainer lines of rice

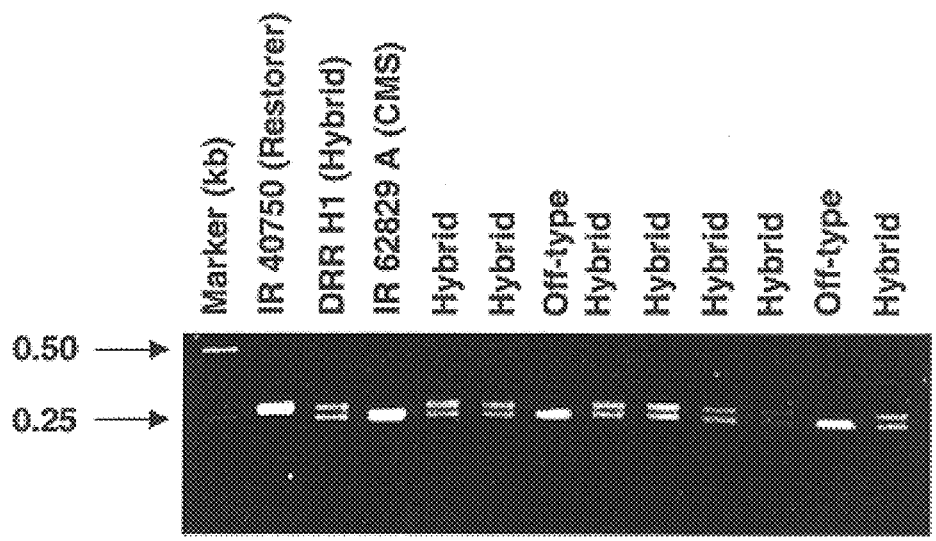
Figure 8. A PCR assay for detecting purity of rice hybrids

DNA MARKERS FOR ASSESSING SEED PURITY AND METHOD OF USING DNA SEQUENCES FOR ASSESSING SEED PURITY

FIELD OF THE INVENTION

The invention relates to a method of using DNA sequences for assessing seed purity. More specifically, the invention relates to a DNA sequences having homology to rice mitochondrial DNA and being unique to Wild Abortive (WA) cytoplasm containing cytoplasmic male sterile lines of rice, and the use of these sequences in a Polymerase Chain Reaction (PCR) assay to distinguish Male Sterile (CMS) lines of rice from their cognate Male Fertile Maintainer Lines. This invention relates to a method for ensuring the purity of cytoplasmic male sterile lines of rice using DNA based markers

BACKGROUND OF THE INVENTION

Hybrid vigor is the phenomenon by which the progeny of a cross between two inbred lines has higher yield potential than either one of the parents. Hybrids can yield upto 10–30% more than the best variety and are a favored option for increasing yield.

Rice is a major cereal crop all over the world; and in many parts of Asia it is the staple part of the diet. It has been estimated that in a number of Asian countries like India rice yields must double by the year 2025 to meet the demands of the increasing population (Hossain, 1996. In Khush (ed) Rice Genetics III, Proc. Third Intl. Rice Genet. Symp., Los Banos Manila, the Philippines. Oct. 16–20, 1995. International Rice Rearch Institute, Manila, the Philippines). As has been demonstrated in the People's Republic of China, where almost fifty percent of the area under rice cultivation is covered by hybrids, the widespread cultivation of hybrid rice is a readily available option for increasing yield. By comparison, in countries like India the area under hybrid rice is less than 1% of the total area under rice cultivation. This illustrates the tremendous potential for increasing the area under hybrid rice cultivation and it is expected that the market for hybrid rice seeds will increase in a number of rice growing countries, including in India.

The most widely used system for hybrid rice production is the three line system (FIG. 1). The three lines include: 1. a male sterile, female fertile line called the Cytoplasmic Male Sterile (CMS) line because it carries a male sterility conferring mutation in the cytoplasmic component of the genome, 2. a maintainer line and 3. a restorer line; the maintainer and restorer lines are male fertile as well as female fertile. The CMS and Maintainer lines are practically identical with respect to the nuclear component of the genome (and are often referred to as iso-nuclear lines) but differ from each other with respect to the cytoplasmic component of the genome. The male sterility of the CMS line is maternally inherited and is most likely due to a mutation in the mitochondrial DNA. The CMS line, being female fertile, can be propagated by fertilization with pollen emanating from the Maintainer line. Since the cytoplasmic component of the genome is not transferred through pollen, the progeny of such a cross would inherit the cytoplasm only from the CMS line and would therefore be male sterile. The nuclear component of the genome of the progeny would also be identical to that of the CMS line, even though half of it is inherited from the Maintainer line, as there is no difference between these two lines with respect to this component of the genome.

The hybrid seeds are produced in a cross of the CMS line with another inbred parental line, called the Restorer line, which as indicated above is Male fertile and Female fertile. In this cross the CMS line serves as the female parent while the Restorer line is the male parent. The Restorer line also carries a Rf (restorer of fertility) gene/s in it's nuclear genome which will restore male fertility to a plant whose cytoplasm has been inherited from the CMS line. The hybrid seeds produced in the cross depicted in FIG. 1 would therefore be fertile. The CMS and Restorer lines are appropriately chosen such that the hybrids exhibit sufficient hybrid vigor (or heterosis) to produce substantially higher yields than inbred varieties.

The vast majority (90% or more) of the rice hybrids that are currently under commercial cultivation in the world derive their cytoplasm from a single source (Yuan, 1995. Hybrid rice seed production technology, Directorate of Rice Research, Hyderabad, India). This cytoplasm, called the WA (wild abortive) cytoplasm, was discovered in a wild rice plant in China. Subsequently, this cytoplasm has been crossed into several different nuclear genetic backgrounds by repeated back-crossing using the recurrent parent as the male donor. In this manner several different CMS lines have been developed, each of which has in turn been crossed with different Restorer lines to develop a number of hybrids, all of which share the same WA cytoplasm.

It is important to maintain the purity of hybrids as any impurities therein would reduce the expected yield. It has been estimated that for every one-percent impurity in the hybrid seed the yield reduction is to the tune of 100 Kg per hectare (Mao et al, 1996 In Virmani, S. S., E. A. Siddiq, and K. Muralidharan (eds) Advances in Hybrid Rice Technology. Proc. Third Intl. Symp. on Hybrid Rice, Directorate of Rice Research, Hyderabad, India). The Indian seed act prescribes that, for hybrid rice, the expected purity should be 98% (Verma, 1996. Seed Tech. News 24:1–4); in the People's Republic of China it is mandated that the purity of hybrid rice should be at least 96% (Wengui Yan, 2000. U.S. Pat. No. 6,066,779). In order to ensure the required levels of hybrid seed purity, the parental lines that are employed in hybrid seed production should have a very high (almost 99%) level of purity.

One of the common admixtures that occur during hybrid seed production is that of Maintainer lines with those of the CMS lines. As these are iso-nuclear lines, it is very difficult to distinguish between these lines based on morphological criteria i.e. other than male sterility which can only be judged at the time of flowering. DNA markers that distinguish the CMS and maintainer lines can be developed and applied at the seedling level for the practical detection of seeds of Maintainer lines that occur as contaminants within stocks of the CMS lines. DNA Markers based on the use of the Polymerase Chain Reaction would be ideally suited for this purpose as they are much more efficient for handling large numbers of samples than hybridization based methods like Restriction Fragment Length Polymorphisms.

The Polymerase Chain Reaction is based on the use of short oligonucleotide sequences as primers for the enzymatic amplification of DNA sequences that occur between two appropriately spaced primer binding sites on the target DNA. The PCR works most reproducibly when the oligonucleotide primers are designed on the basis of a knowledge of the target DNA sequence. Protocols have been developed for PCR which are based on the use of short (8–10 bases long), randomly designed oligonucleotide primers (Williams et al, 1990; Nucleic acids research 18: 6531–6535). These primers are not based on a knowledge of the target DNA sequence and kits containing large numbers of these randomly generated primers are now commercially available. The DNA markers that are developed by this method are known as Randomly Amplified Polymorphic DNA (RAPD) Markers. Because a large number of primers are available, genetic polymorphisms can be detected by this method, even within closely related lines. However, the reproducibility of RAPD markers is poor due to the short length of the oligonucleotide (RAPD) primers and possibly also due to the lack of the required degree of specificity for the target. This severely limits the practical application of RAPD markers, as diagnostic markers for distinguishing different genotypes.

RAPD markers that distinguish CMS (WA cytoplasm) and Maintainer lines of rice have been described (Jena and Pandey 1999; Hybrid Rice Newsletter. 2: 13–14). However, the low reproducibility of these markers has made it practically impossible to apply them in a routine manner for distinguishing CMS and Maintainer lines. There is thus a need for the development of reproducible PCR based methods that can be applied for distinguishing the CMS and Maintainer lines. The desired level of reproducibility can be obtained if the oligonucleotide primers are based on a knowledge of the sequence of a region of rice DNA that is polymorphic between the CMS and Maintainer lines. PCR assays based on such primers would be highly reproducible because these primers would be longer in length than the primers used in RAPD analysis and would be specific for the target DNA sequence.

In this application, is described the identification and sequence determination of a region of rice mitochondrial DNA that is specific to CMS lines of rice containing the wild abortive (WA) type of cytoplasm. Based on this sequence, specific oligonucleotide primers have been developed that can be used in a PCR assay to distinguish CMS (WA) lines from their iso-nuclear Maintainer lines. These primers have been used to distinguish several different CMS lines (all containing the WA cytoplasm) of rice from their cognate Maintainer lines. In a coded test, this assay was used to predict with 100% accuracy the genotypes of a mixture of CMS (WA) and Maintainer lines of rice. The assay can therefore be used by rice breeders to successfully detect admixtures of Maintainer lines in seed stocks of the CMS line, thereby ensuring the purity of this parental line and the hybrid derived from it.

Another source of impurity within the seed stocks of the CMS line is caused by cross pollination with pollen emanating from rice plants that are not the designated Maintainer line. A minimum isolation distance of 300 meters is prescribed for multiplication of rice CMS lines (Virmani, 1993. Advances in Agronomy 57:377–462) i.e. within this distance no rice lines other than the Maintainer line (the preferred pollen donor or male parent) should be cultivated. This is based on the observation that pollen originating from rice plants growing beyond this distance will not pollinate the female parent. Occasionally, this minimum isolation distance is either not strictly followed or local conditions (for e.g. wind flow and weather) might permit pollen to be transferred from plants that are growing beyond the 300 meters distance. Therefore, it is. important to monitor the extent of outcrossing with rogue pollen donors that has occurred during the multiplication of the CMS lines. In this patent, are described methods for the application of sequence specific PCR markers like microsatellites and Sequence Tagged Sites (STSs) towards estimating the extent of outcrossing that has occurred during the multiplication of seed stocks of the CMS line.

Although the application is for estimating the extent of outcrossing that has occurred for CMS lines of rice, a similar approach can be used for estimating the extent of outcrossing that has occurred within the CMS lines of other crops including but not limited to maize, pearl millet, sorghum, wheat, sunflower, mustard, cabbage, cauliflower, tomato, pepper, okra, etc wherein the CMS lines are used for the production of hybrids and appropriate microsatellite or STS markers are available.

The estimation of hybrid seed purity is conventionally done by the grow out test (GOT), which is based on the assessment of morphological and floral characteristics (that distinguish the hybrid) in a representative sample of plants that are grown to maturity. Rice plants take several months to reach maturity and the seeds have to be stored under appropriate conditions as they cannot be marketed until these results become available. In addition substantial delays can result, as occurs in India, if the first growing season after hybrid seed production which is taken up by the GOT is also the preferred season for hybrid cultivation. In such cases, the seeds have to be stored for upto a year i.e. until the subsequent growing season before they can be marketed. For seed companies, large amounts of capital are therefore locked up in the form of hybrid seed stock for prolonged periods while awaiting the results of the GOT. Another disadvantage of the GOT is that it can be subjective due to environmental influences on the expression of morphological characteristics. Further, there is also the possibility that adverse climatic conditions (like heavy wind or rain) can damage or destroy the crop and make it difficult to collect the data.

With the objective of replacing the GOT with a test that is superior in terms of speed and accuracy, a PCR based assay is described for assessing hybrid seed purity. This test involves the use of either microsatellite or STS (Sequence Tagged Site) polymorphisms that distinguish the parental lines of rice hybrids. These polymorphisms are co-dominant and the alleles are detected as DNA fragments of different sizes following PCR and agarose gel electrophoresis. The hybrid can be identified because it will have alleles contributed by both parents i.e. PCR amplified fragments of two different sizes will be obtained after use of the DNA isolated from the hybrid plant as a template in PCR. One of these alleles will be contributed by the male sterile, female fertile (CMS) parent while the other will be contributed by the male fertile, female fertile (Restorer) parent. This test can be conducted on DNA isolated from six day old rice seedlings and the assay can be completed within forty eight hours. The implementation of this PCR based test for seed purity will result in considerable savings for the seed industry. Additional modifications of this assay are described wherein the test need not be conducted on individual seedlings but can be conducted on populations of seedlings obtained from the hybrid seed stock.

SUMMARY OF THE INVENTION

This invention relates to novel DNA markers for assessing seed purity and a method for ensuring the purity of cytoplasmic male sterile lines of rice using DNA based markers. This method is based on the identification of a DNA Sequence that is specific to WA cytoplasmic male sterile lines of rice and the development of specific DNA markers derived from the same. These DNA markers can be used to detect admixtures of male fertile Maintainer lines with CMS lines. This application is likely to be very beneficial to the hybrid rice industry as admixtures of the type described above often lead to reduced purity of the hybrid seeds and poor performance of the product in the marketplace. Methodology for the application of co-dominant sequence specific PCR markers like microsatellites and STSs for detecting impurities in parental lines and hybrids of rice and other crops is also provided.

DETAILED DESCRIPTION OF THE INVENTION

Rice is a major cereal crop in many parts of the world. Yield increases of 10–30% are reported following cultivation of hybrid rice in the People's Republic of China where it is being practised on a large scale. It is expected that, in the near future, hybrid rice technology will also be practised on a large scale in a number of other rice growing countries. Currently, most rice hybrids are produced through a three line system comprising of: 1. a Cytoplasmic Male Sterile (CMS) line that is female fertile but is male sterile due to a mutation in the cytoplasmic (most probably the mitochondrial) component of the rice genome; 2. a male fertile, female fertile Maintainer line that is identical to the CMS line with respect to the nuclear component of the genome but has a different cytoplasmic genotype that does not induce male sterility; 3. a male fertile, female fertile Restorer line. The CMS line serves as the female parent for the hybrid while the Restorer line is the male parent. During hybrid seed production the CMS and Restorer lines are cultivated in close proximity to each other such that pollen emanating from the Restorer line will pollinate the flowers of the CMS line. As the CMS line is male sterile it will not set seed by self pollination and any seeds that are formed on the CMS line are deemed to have arisen as a consequence of fertilisation with pollen emanating from the Restorer line. The restorer line carries one or more nuclear encoded genes that will restore male fertility to the hybrid even though it carries the CMS cytoplasm. Thus the hybrid is self fertile.

The CMS line cannot be propagated by selfing as it is male sterile. Instead, the propagation of the CMS lines is accomplished by using the CMS line as a female parent and the Maintainer line as the male parent. The genotype of the progeny that arise from this cross will be identical to the genotype of the CMS line as the Maintainer lines are practically identical to the CMS line with respect to the nuclear component of the genome. The progeny will have the male sterile characteristic of the CMS line because the cytoplasmic component of the genotype is contributed by the female parent; which in this case is the CMS line. It is also pertinent to note that the Maintainer line does not carry any Restorers of the Cytoplasmic Male Sterile phenotype of the CMS line.

The identity of the nuclear genotype of the CMS and Maintainer lines means that the two lines are almost indistinguishable by morphological criteria. This creates a practical problem because it is very difficult to detect admixtures of the Maintainer line within seed stocks of the CMS line. Since the Maintainer lines are self fertile, these impurities can produce seeds in a hybrid rice production field without the necessity for fertilization with the Restorer line. This leads to a contamination of the seeds of the Maintainer line with those of the hybrid. This type of a contamination is one of the most frequently observed during hybrid rice seed production and leads to a reduction in the expected yield and poor performance of the hybrid in the field. If the purity of the hybrid is less than the mandatory limit fixed by Seed Certification agencies, this is 98% in India and 96% in China, the entire seed lot is rejected leading to considerable loss for the seed producers (companies).

The vast majority of the CMS lines that are employed in commercial production of hybrid rice are based on the use of the WA cytoplasm. In this patent we describe the identification of a DNA sequence that is unique to rice lines containing the WA cytoplasm and is highly homologous to rice mitochondrial DNA. Sequence Specific oligonucleotide primers have been developed based on this DNA sequence that can be used in a PCR assay to reliably distinguish rice cytoplasmic male sterile lines containing the WA cytoplasm from their cognate Maintainer lines. These primers can therefore be used by hybrid rice breeders/seed companies to detect impurities of the Maintainer line within the CMS line. By ensuring purity of the CMS lines, a major source of contamination of the hybrid seeds is removed leading to obvious benefits for the seed industry and farmers.

BRIEF DESCRIPTION OF THE ACCOMPANYING DRAWINGS

FIG. 1. The three line system for hybrid rice production

This figure is a graphic of how a hybrid is produced in a three line system. Cytoplasmic male sterile (CMS) line (pollen sterile), which serves as the female parent is crossed with the Maintainer line (pollen fertile) which serves as the male parent. CMS and Maintainer lines are iso-nuclear except for the pollen sterility in CMS lines hence Maintainers are necessary for propagation of the CMS lines. Once CMS lines are obtained, they are crossed with a Restorer line which can possess any number of desirable agronomic traits and which also restores fertility to the progeny. Therefore the hybrid produced by such a cross is fertile.

FIG. 2. PCR amplification of a DNA sequence that is specific to CMS lines of rice PCR was performed as described in Example 3 using microsatellite primer RM9 (SEQ ID No. 6 and SEQ ID No. 7). The PCR products were separated on a 2% agarose gel, stained with ethidium bromide and visualized under ultraviolet light. Lane 1 contains a DNA molecular weight marker [(λDNA digested with Hind III (New England Biolabs, USA)]; lane 2 contains PCR amplified product of a Maintainer line (IR 62829 B); lane 3, the hybrid (DRR H1) and lane 4, CMS line (IR 62829 A). An extra DNA band which is present only in the hybrid and CMS line, but absent in the Maintainer line is indicated by the black arrow on the right hand corner of the gel.

FIG. 3. Nucleotide sequence of a rice CMS line specific DNA. (SEQ ID No. 1)

A CMS specific DNA band that was identified using microsatellite primer RM9 was purified as described in Example 4. The DNA band was sequenced using an automated DNA sequencer (ABI 3700; ABI, Foster City, USA). The sequence is composed of 325 bases. Homology search revealed that it has high homology to the rice mitochondrial DNA, DBJ Accession #D21251 except for a small stretch from base positions 1 to 36. PCR primers were designed based on this sequence information to obtain amplification only in CMS lines; the Forward primer was based on the-region which does not exhibit homology to the rice mitochondrial DNA (position 1 to 36) and the Reverse primer was based on the mitochondrial DNA sequence.

FIG. 4. Homology of CMS specific DNA sequence with rice mitochondrial DNA (SEQ ID No. 2).

The DNA sequence information obtained by sequencing as described in Example 4 was aligned with the rice motochondrial DNA, DBJ Accession #D21251 using the Boxshade server available at http:/www.ch.embnet.org/software/BOX_form.html FIG. 5. A PCR assay for distinguishing CMS and Maintainer lines of rice.

PCR products amplified using the SEQ ID No. 4 and SEQ ID No. 5 were separated on a 1% agarose gel, stained with ethidium bromide and visualized under ultraviolet light. Lane 1 is a kilobase DNA marker. Lane 2 contains IR58025 A (CMS); lane 3, DRR H2 (hybrid); lane 4, IR 58025 B (Maintainer); lane 5, IR 62829 A (CMS); lane 6, DRR H1 (hybrid); lane 7, IR 62829 B (Maintainer). Three other sets of CMS-Maintainer lines were analysed and in all cases, amplification was observed only in the CMS lines and hybrids but not observed in the Maintainer lines.

FIG. 6. Detection of Restriction Fragment Length Polymorphisms (RFLP) between CMS and Maintainer lines of rice using CMS specific DNA sequence as a probe.

Genomic DNA isolated from IR 58025 A (CMS) and IR 58025 B (Maintainer) were digested with EcoR V restriction enzyme and separated on an agarose gel overnight. Southern hybridization was performed as described in Example 7 using the CMS specific DNA fragment as a probe. The probe hybridized to a 2.3 kb region in the IR 58025 A (CMS) line whereas in the IR 58025 B (Maintainer) line it hybridized to a 0.6 kb region.

FIG. 7. A multiplex PCR assay for distinguishing CMS and Maintainer lines of rice.

Lane 1 is a DNA molecular weight marker [(λDNA digested with Hind III (New England Biolabs, USA)]; lane 2, IR 58025 A (CMS); lane 3, IR 58025 B (Maintainer). Samples in lane 2 and 3 are PCR products amplified by SEQ ID No. 4 and SEQ ID No. 5 alone. Lane 4, IR 58025 A (CMS); lane 5, IR 58025 B (Maintainer). Samples in lane 4 and 5 are PCR products amplified by multiplexing SEQ ID No. 4, SEQ ID No. 5, SEQ ID No. 8 and SEQ ID No. 9. The monomorphic fragment is the PCR product of SEQ ID No. 8 and SEQ ID No. 9 and the polymorphic fragment is the PCR products of SEQ ID No. 4, SEQ ID No. 5.

FIG. 8. A PCR assay for detecting purity of rice hybrids.

Lane 1, is a 1 kb DNA molecular weight marker. PCR was performed using primers for the RM164 microsatellite locus Lane 2 is IR 40750 (Restorer), lane 3 is DRR H1 (hybrid) and lane 4 is IR 62829 A (CMS). Note that a single polymorphic PCR amplified fragment is observed in lanes 2 and 4. The hybrid exhibits two DNA fragments which are characteristic of the alleles contributed by both parents. Lane 5–12 represent a PCR assay performed to determine the purity of seeds from a stock of the DRR H1 hybrid. The presence of two bands indicates that lanes 5, 6, 8, 9, 10, 11 and 13 represent true hybrids. The presence of a single band indicates that the plants represented by lanes 7 and 12 (off-types) are impurities.

In short, the invention provides a DNA sequence (SEQ ID No.1 & SEQ ID No 3) substantially homologous to rice mitochondrial DNA, said sequence being unique to Wild Abortive (WA) cytoplasm containing cytoplasmic male sterile lines of rice. The invention also provides oligonucleotide primers (SEQ ID No.4 & SEQ ID No 5) based on this DNA sequence in a Polymerase Chain Reaction (PCR) assay to distinguish Male Sterile (CMS) lines of rice from their cognate Male Fertile Maintainer Lines.

Further, the invention provides a method of using oligonucleotide primers (SEQ ID No.4 & SEQ ID No 5) based on this DNA sequence in a Polymerase Chain Reaction (PCR) assay to distinguish Male Sterile (CMS) lines of rice from their cognate Male Fertile Maintainer Lines.

In an embodiment, the invention provides a method of using oligonucleotide primers having SEQ ID No.4 & SEQ ID No 5 based on this DNA sequence in a Polymerase Chain Reaction (PCR) assay to distinguish Male Sterile (CMS) lines of rice from their cognate Male Fertile Maintainer Lines when the said Male Sterile Lines contain the WA (wild abortive) cytoplasm.

In an embodiment, the invention provides a method of using oligonucleotide primers having SEQ ID No.4 & SEQ ID No 5 based on the DNA sequence in a Polymerase Chain Reaction (PCR) assay to distinguish WA Cytoplasmic Male Sterile (CMS) lines of rice from their cognate Male Fertile Maintainer Lines wherein a DNA amplification product is obtained if the template DNA is from the CMS line and a DNA amplification product is not obtained if the template DNA is from the cognate Male Fertile Maintainer line.

In another embodiment, the invention provides method of using primers having SEQ ID No.4 & SEQ ID No 5 based on this DNA sequence in a Polymerase Chain Reaction (PCR) Assay to distinguish WA Cytoplasmic Male Sterile lines of rice from their cognate Male Fertile Maintainer lines wherein detection of the PCR amplified fragment/s is by agarose gel electrophoresis followed by Ethidium bromide staining.

In still another embodiment, the invention provides a method of using primers having SEQ ID No.4 & SEQ ID No 5 based on this DNA sequence this in a Polymerase Chain Reaction (PCR) Assay to distinguish WA Cytoplasmic Male Sterile lines of rice from their cognate Male Fertile Maintainer lines wherein detection of the PCR amplified fragment/s is by detection of a radioactively labeled nucleotide that is incorporated into the PCR amplified product.

In yet another embodiment, the invention provides a method of using primers having SEQ ID No.4 & SEQ ID No 5 based on this DNA sequence in a Polymerase Chain Reaction (PCR) Assay to distinguish WA Cytoplasmic Male Sterile lines of rice from their cognate Male Fertile Maintainer lines wherein a non-radioactively labeled nucleotide is incorporated into the PCR amplified product and detection is by colorimetry, chemiluminescence, or measurement of fluorescence.

In another embodiment, the invention provides a method of using primers having SEQ ID No.4 & SEQ ID No 5 based on this DNA sequence in a PCR-ELISA (Enzyme Linked Immunosorbent Assay) format to distinguish WA Cytoplasmic Male Sterile lines of rice from their cognate Male Fertile Maintainer lines, the said PCR-ELISA format may involve; (a). use of a labeled capture probe or one labeled PCR primer that can be bound to suitably coated solid surface made of polystyrene, styrene, glass, etc., (b) use of non-radioactively labeled [the label being digoxigen (DIG), flourescein, etc.] nucleotides in the PCR and subsequent detection with anti-DIG or anti-flourescein antibodies that are conjugated to enzymes used for ELISA like horseradish peroxidase, alkaline phosphatase, beta-galactosidase, glucose oxidase, etc; modifications of the PCR-ELISA format, including alternate methods for labeling the PCR amplified fragment, attachment of probe to solid surfaces, methods of detection, etc In an embodiment, the invention provides a method of using primers having SEQ ID No.4 & SEQ ID No 5 based on this DNA sequence in a PCR Assay to distinguish WA Cytoplasmic Male Sterile lines of rice from their cognate Male Fertile Maintainer lines wherein the method of detection is based on the use of flourescently labelled nucleotides in Fluorescence Resonance Energy Transfer (FRET) based detection systems including Taqman, Molecular Beacon, etc which are familiar to those conversant with prior art.

In an embodiment, the invention provides a method of using a multiplex PCR assay of a first pair of oligonucleotide primers having SEQ ID No.4 & SEQ ID No 5 based on this DNA sequence, in conjunction with a second pair of oligonucleotide primers, wherein a DNA amplification product is obtained using the first pair of primers only if the template DNA is obtained from the WA Cytoplasmic Male Sterile lines but not from the Male Fertile Maintainer Line; and another DNA amplification product is obtained using the second set of primers irrespective of whether the template DNA is from a CMS or a Male Fertile Maintainer Line, this second pair of oligonucleotide primers can be derived from any sequenced portion of the rice genome outside the region targeted by the first primer pair, another consideration is that successful amplification of the respective target DNA Sequences should occur even when the two primer pairs are included in the same PCR mixture. The sequences of several oligonucleotide primer pairs that belong to this second set and can be successfully multiplexed in a PCR assay with the first set of oligonucleotide primer pairs.

In yet another embodiment, the invention provides a method of using CMS specific DNA sequence in a Southern hybridization assay (using either radioactive or non-radioactive labeling methods) to distinguish WA Cytoplasmic Male Sterile Lines of rice from their cognate Male Fertile Maintainer lines.

In still another embodiment, the invention provides a method of using co-dominant sequence specific DNA markers like micro-satellites and Sequence tagged Sites (STSs) in a Polymerase Chain Reaction Assay for assessing the extent of out-crossing with rogue pollen donors (i.e. rice lines that are not the designated Maintainers) and consequent occurrence of genetically impure seeds during the multiplication of Cytoplasmic Male Sterile lines of rice. In yet another embodiment, the invention provides a method wherein the DNA is isolated from single seedlings, PCR analysis is performed and the genotype is assessed by electrophoresis on agarose gels or polyacrylamide gels and detection is either by ethidium bromide staining, silver staining or methods of detection that are applicable if either a radioactive label or a non-radioactive fluorescent label is incorporated into the PCR amplified fragment.

In an embodiment, the invention provides a method of using co-dominant sequence specific DNA markers like micro-satellites and Sequence tagged Sites (STSs) in a Polymerase Chain Reaction Assay for assessing the extent of out-crossing with rogue pollen donors (i.e. rice lines that are not the designated Maintainers) and consequent occurrence of genetically impure seeds during the multiplication of Cytoplasmic Male Sterile lines of rice wherein the DNA is isolated from a population of seedlings (a typical number of individuals within the population could be a 100) that are obtained by germinating seeds of the CMS stock, PCR analysis is performed, and the extent of impurities is judged by estimating allele frequencies within the population at the locus that is being assessed. The method of estimating allele frequencies within the population involves separation of flourescently labeled PCR amplified fragments by gel electrophoresis and estimation of the heights of the peaks that correspond to specific alleles.

In an embodiment, the invention provides a method of using co-dominant sequence specific DNA markers like micro-satellites and STSs in a Polymerase Chain Reaction Assay for assessing the extent of out-crossing with rogue pollen donors (i.e. lines that are not the designated Maintainers) and consequent occurrence of genetically impure seeds during the multiplication of Cytoplasmic Male Sterile lines of any crop or economically valuable plant in which the three line system of hybrid production is followed. The DNA is isolated from single seedlings, PCR analysis is performed and the genotype is assessed by electrophoresis on agarose gels or polyacrylamide gels and detection is either by ethidium bromide staining, silver staining or methods of detection that are applicable if either a radioactive label or a non-radioactive fluorescent label is incorporated into the PCR amplified fragment.

In still another embodiment, the invention provides a method of using co-dominant sequence specific DNA markers like micro-satellites and STSs in a Polymerase Chain Reaction Assay for assessing the extent of out-crossing with rogue pollen donors (i.e. lines that are not the designated Maintainers) and consequent occurrence of genetically impure seeds during the multiplication of Cytoplasmic Male Sterile lines of any crop or economically valuable plant in which the three line system of hybrid production is followed and the DNA is isolated from a population of seedlings (a typical number of individuals within the population could be a 100) that are obtained by germinating seeds of the CMS stock, PCR analysis is performed, and the extent of impurities is judged by estimating allele frequencies within the population at the locus that is being assessed. The method of estimating allele frequencies within the population would involve separation of flourescently labeled PCR amplified fragments by gel electrophoresis and estimation of the heights of the peaks that correspond to specific alleles.

In an embodiment, the invention provides a method of using co-dominant sequence specific DNA markers like micro-satellites and STSs in a Polymerase Chain Reaction Assay for assessing the extent of purity of parental lines of rice hybrids wherein a two line system for hybrid rice production is followed. These parental lines include a female parent that has conditional male sterility wherein sterility is induced by temperature, photoperiod, treatment with chemicals that induce lethality of the male gametes etc. The DNA is isolated from single seedlings, PCR analysis is performed and the genotype is assessed by electrophoresis on agarose gels or polyacrylamide gels and detection is either by ethidium bromide staining, silver staining or methods of detection that are applicable if either a radioactive label or a non-radioactive fluorescent label is incorporated into the PCR amplified fragment.

In another embodiment, the invention provides a method of using co-dominant sequence specific DNA markers like micro-satellites and STSs in a Polymerase Chain Reaction Assay for assessing the extent of purity of parental lines of rice hybrids wherein a two line system for hybrid rice production is followed. These parental lines include a female parent that has conditional male sterility wherein sterility is induced by temperature, photoperiod, treatment with chemicals that induce lethality of the male gametes, etc. What is claimed is a method wherein the DNA is isolated from a population of seedlings (a typical number of individuals within the population could be a 100) that are obtained by germinating seeds of the parental lines, PCR analysis is performed, and the extent of impurities is judged by estimating allele frequencies within the population at the locus that is being assessed. One method of estimating allele frequencies within the population would involve separation of flourescently labeled PCR amplified fragments by gel electrophoresis and estimation of the heights of the peaks that correspond to specific alleles.

In yet another embodiment, the invention provides a method of using co-dominant sequence specific DNA markers like micro-satellites and STSs in a Polymerase Chain Reaction Assay for assessing the extent of purity of parental lines of hybrids of any economically important crop wherein a two line system for hybrid production is followed; these parental lines include a female parent that has conditional male sterility wherein sterility is induced by temperature, photoperiod, treatment with chemicals that induce lethality of the male gametes, etc. The DNA is isolated from single seedlings, PCR analysis is performed and the genotype is assessed by electrophoresis on agarose gels or polyacrylamide gels and detection is either by ethidium bromide staining, silver staining or methods of detection that are applicable if either a radioactive label or a non-radioactive fluorescent label is incorporated into the PCR amplified fragment. In an embodiment, the invention provides a method of using co-dominant sequence specific DNA markers like micro-satellites and STSs in a Polymerase Chain Reaction Assay for assessing the extent of purity of parental lines of hybrids of any economically important crop wherein a two line system for hybrid production is followed. These parental lines include a female parent that has conditional male sterility wherein sterility is induced by temperature, photoperiod, treatment with chemicals that induce lethality of the male gametes, etc. What is claimed is a method wherein the DNA is isolated from a population of seedlings (a typical number of individuals within the population could be a 100) that are obtained by germinating seeds of each of the parental lines, PCR analysis is performed, and the extent of impurities is judged by estimating allele frequencies within the population at the locus that is being assessed. Estimating allele frequencies within the population would involve separation of flourescently labeled PCR amplified fragments by gel electrophoresis and estimation of the heights of the peaks that correspond to specific alleles.

In an embodiment, the invention provides a method of using co-dominant sequence specific DNA markers like micro-satellites and STSs in a Polymerase Chain Reaction Assay for assessing purity of hybrid seeds when the seeds (or plants) are of rice and either a Three line or Two line system is used for hybrid production. The DNA is isolated from single seedlings, PCR analysis is performed and the genotype is assessed by electrophoresis on agarose gels or polyacrylamide gels and detection is either by ethidium bromide staining, silver staining or methods of detection that are applicable if either a radioactive label or a non-radioactive fluorescent label is incorporated into the PCR amplified fragment.

In an embodiment, the invention provides a method of using co-dominant sequence specific DNA markers like micro-satellites and STSs in a Polymerase Chain Reaction Assay for assessing purity of hybrid seeds when the seeds (or plants) are of rice and either a Three or Two line system is used for hybrid production; and the DNA is isolated from a population of seedlings (a typical number of individuals within the population could be 400) that are obtained by germinating seeds of the hybrid stock, PCR analysis is performed, and the extent of impurities is judged by estimating allele frequencies within the population at the locus that is being assessed. Estimating allele frequencies within the population would involve separation of flourescently labeled PCR amplified fragments by gel electrophoresis and estimation of the heights of the peaks that correspond to specific alleles.

In an embodiment, the invention provides a method of using co-dominant sequence specific DNA markers like SSRs and STSs in a Polymerase Chain Reaction Assay for assessing purity of hybrid seeds when the seeds (or plants) are of any crop or economically valuable plant and either a Three or Two line system is used for hybrid production. The DNA is isolated from single seedlings, PCR analysis is performed and the genotype is assessed by electrophoresis on agarose gels or polyacrylamide gels and detection is either by ethidium bromide staining, silver staining or methods of detection that are applicable if either a radioactive label or a non-radioactive fluorescent label is incorporated into the PCR amplified fragment.

In an embodiment, the invention provides a method of using co-dominant sequence specific DNA markers like SSRs and STSs in a Polymerase Chain Reaction Assay for assessing purity of hybrid seeds when the seeds (or plants) are of any crop or economically valuable plant and either a Three or Two line system is used for hybrid production; and the DNA is isolated from a population of seedlings (a typical number of individuals within the population could be 400) that are obtained by germinating seeds of the hybrid stock, PCR analysis is performed, and the extent of impurities is judged by estimating allele frequencies within the population at the locus that is being assessed. Estimating allele frequencies within the population would involve separation of flourescently labeled PCR amplified fragments by gel electrophoresis and estimation of the heights of the peaks that correspond to specific alleles.

To describe the invention in detail, initially, a PCR assay was performed on template DNA individually isolated from a set of rice lines that constitute the CMS (WA cytoplasm), Maintainer and the corresponding hybrid using oligonucleotide primers that amplify the RM9 rice microsatellite locus (McCouch et al., 1996. Rice Genetics III, Proc. Third Intl. Rice Genet. Symp. Los Banos Manila, the Philippines. Oct. 16–20, 1995. International Rice Research Institute, Manila, the Philippines). The PCR amplified fragments were separated by agarose gel electrophoresis and detected by staining with ethidium bromide. As expected for a PCR assay in which the RM9 locus is assayed, a PCR amplified fragment of approximately 250 bp was observed using template DNA from all three lines (FIG. 2). Besides this, a PCR amplified fragment of approximately 350 bp was observed only in reactions in which the template DNA was obtained from either the CMS line or the hybrid (FIG. 2). However, PCR amplification of this fragment was found to be highly sensitive to reaction conditions and was often not observed even when the template DNA was from either CMS lines or hybrids. This indicated that primers directed against the RM9 microsatelite locus could not be reliably used to distinguish CMS and maintainer lines. We think that this lack of reproducibility arises due to imperfect pairing between the RM9 primers and the target sequence in the lines containing the CMS cytoplasm.

Subsequently, the CMS line specific PCR amplified fragment (size 325 bp) indicated in FIG. 2 was purified and it's nucleotide sequence was determined on an automated DNA sequencer by using the Forward and Reverse oligonucleotide primers from the RM9 locus. The nucleotide sequence of the PCR amplified fragment is indicated in FIG. 3.

A search for homologous DNA sequences in the GenBank DNA database was performed using the BLAST algorithm (Altschul et al., 1997. Nucleic Acids Res. 25: 3389–3402) through the web site of the National Center for Biotechnology Information, Bethesda, Md., USA. The said DNA sequence is highly homologous to one particular entry [accession #D21251; DNA database of Japan (DBJ), hereby incorporated as a reference] in the database. This entry is a sequence of rice (*Oryza sativa*) mitochondrial DNA originating from a genomic region encoding genes for ribosomal protein S3, L16, S12 and NADH dehydrogenase subunit 3. The extent of homology of the said DNA sequence to rice mitochondrial DNA is depicted in FIG. 4. It is clear that the regions are highly homologous excepting a stretch of DNA

[corresponding to nucleotides ACGGCCCTCATCACCT-TCTTTCACTTTTTGTTTTTG (SEQ ID No. 3)] that is absent in the sequence of rice mitochondrial DNA deposited as accession #D21251.

Based on this sequence, one pair of oligonucleotide primers (Table 2 shown at the end of the description) that can be used in a PCR assay to distinguish CMS (WA) and Maintainer lines of rice was designed. One of the primers (Forward primer) is based on the sequence that is specific to the CMS lines (FIG. 3) while the other primer (Reverse primer) is based on the sequence of rice mitochondrial DNA in the genomic region upstream of the gene for ribosomal protein S3 between nucleotide #s1362 and 1384 as indicated in DBJ accession #D21251. The oligonucleotide primers [Forward 5'-ACTTTTTGTTTTTGTGTAGG-3' (SEQ ID No. 4); Reverse 5'-TGCCATATGTCGCTTAGACTTTAC-3' (SEQ ID No. 5)] were used in a PCR assay with template DNA from the CMS and Maintainer lines of rice that are listed in Table 1 (shown at the end of the description). A PCR amplified product of 325 bp was obtained (FIG. 5) using the primers SEQ ID No. 4 and SEQ ID No. 5 when the template DNA was isolated from the CMS lines (IR 58025 A, IR 62829 A, PMS 8 A, PMS 10 A, 78897 A) but was not obtained when the source of the template DNA was the Maintainer lines (IR 58025 B, IR 62829 B, PMS 8 B, PMS 10 B, 78897 B). In a further validation of the assay, a coded test was conducted in which genomic DNA was isolated from 35 different rice plants, 15 of which were of the CMS line IR 58025 A and 20 were of the Maintainer line IR 58025 B. The PCR assay was conducted without a knowledge as to which of these 35 plants are of the CMS line and which are of the Maintainer line. This assay was used to accurately predict the genotype of each of the 35 different plants indicating the applicability of the PCR assay as a method for distinguishing CMS and Maintainer lines of rice.

The said CMS specific PCR amplified fragment was radiolabelled using $\alpha^{32}$p-dATP. Genomic DNAs isolated from cognate pairs of CMS (IR 58025 A and IR 62829 A) and Maintainer (IR 58025 B and IR 62829 B) lines were digested with any one of several different restriction enzymes, separated by agarose gel electrophoresis and hybridized (as described in Sambrook et al. 1989. Cold Spring Harbor, N.Y., USA) to the radiolabelled probe. FIG. 6 indicates that a restriction fragment length polymorphism between CMS (WA) and maintainer lines of rice is detected using this probe and the EcoR V restriction enzyme. Purification of mitochondrial DNAs from CMS and maintainer lines of rice and RFLP analysis using the above mentioned probe-enzyme combination revealed a similar polymorphism confirming that the detected polymorphism is in the mitochondrial DNA. Polymorphisms were also detected using other restriction enzymes that were tested.

A multiplex PCR assay was also developed for distinguishing CMS and Maintainer lines of rice. In this assay, the first set of oligonucleotide primers used in the above mentioned PCR assay were multiplexed with primers belonging to a second set of oligonucleotide primers. This second set of oligonucleotide primers were designed based on either a sequence of rice chromosome I that was obtained as part of the ongoing International Rice Genome Project (and publicly available as GeneBank Accession Number #AP001859; hereby incorporated as reference) or the sequence of rice mitochondrial DNA that is available as DBJ Accession #D21251. This second set of oligonuleotide primers were designed such that any one of the primer pairs belonging to this second set can be added to a PCR assay mixture containing primers belonging to the first set of oligonucleotide primers without affecting the formation of the CMS specific DNA fragment that is amplified by the first set of oligonucleotide primers. In this multiplex PCR' assay, the second set of oligonucleotide primers amplify a specific DNA fragment irrespective of whether the template DNA is from a CMS line or a Maintainer line (FIG. 7). As a PCR amplified fragment is obtained from both the CMS and Maintainer lines, the use of this second set of primers serves as a control for extraneous factors (like inhibitors of PCR, poor quality of the template DNA, etc.) that can affect the outcome of the PCR. The sequences of the second set of oligonucleotide primers, their location within the rice genome and the size of the DNA fragment that is amplified by the use of these primers is indicated in Table 2. (shown at the end of the description).

Microsatellites (also called simple sequence repeats or SSRs) are simple, tandemly repeated di-to tetra-nucleotide sequence motifs flanked by unique sequences. Microsatellites are abundant and well distributed throughout the genome in rice (McCouch et al 1997) as well as many other crop plants (Powell et al, 1996. Trends Plant Sci 1: 215–222). Microsatellites are valuable as genetic markers because they are co-dominant, detect high levels of allelic diversity and are efficiently assayed by the PCR. The current level of average genome-wide coverage provided by microsatellites in rice, one in every 6 cM (Temnykh et al, 2000. Theor. Appl. Genet. 100:697–712) is sufficient to be useful for assessment of hybrid seed purity and for genotype identification. Similar to microsatellites, a STS is a short stretch of genomic sequence that can be detected by PCR and is mapped to a specified site as a landmark in the genome. Some of the STSs mapped in rice are polymorphic (Ghareyazie at al, 1995. Theor. Appl. Genet. 91:218–227; Robenoil et al, 1996. In Khush, G. S. (ed) Rice genetics III. Proc. Third Intl. Rice Genet. Symp. Los Banos Manila, the Philippines. Oct. 16–20, 1995. International Rice Research Institute, Manila, the Philippines.).

A minimum isolation distance of 300 metres is prescribed for multiplication of rice CMS lines (Virmani, 1993. Hybrid rice. Advances in Agronomy 57:377–462) i.e. within this distance no rice lines other than the Maintainer line (the preferred pollen donor or male parent) should be cultivated. This is based on the observation that pollen originating from rice plants growing beyond this distance will not pollinate the CMS line. Occasionally, this minimum isolation distance is either not strictly followed or local conditions (for eg. wind flow and weather) might permit pollen to be transferred from plants that are growing beyond the 300 metres distance.

The extent of cross pollination of CMS lines with rogue pollen originating from rice lines (other than Maintainer line) that are growing in nearby fields can be assessed using Microsatellite or STS markers that are polymorphic between these rice lines and the CMS line. These polymorphic markers are identified by PCR, agarose gel electrophoresis and ethidium bromide staining using template DNA from each of the potential donor lines (in a typical situation this would be between 1–3 lines) and the CMS line. A preferable marker would be one that will detect cross pollination arising from any one of these rogue lines. A plant arising from cross pollination would be detected using such a marker by the presence of heteozygosity (i.e presence of two DNA fragments of different sizes one of which is contributed by the female (CMS) parent while the other is contributed by the male parent (rogue pollen donor). In contrast to this situation, homozygosity (presence of a single DNA fragment) will be observed in the offspring, if pollination occurs, as desired, with pollen emanating from the Maintainer line. This is because the CMS and Maintainer lines are isonuclear to each other; meaning that they are essentially identical to each other with respect to the nuclear DNA markers. The procedure for DNA isolation, PCR and agarose gel electrophoresis is as described in Example 9.

A variation of this assay is also described in Example 9 wherein the DNA is isolated from leaves obtained from a population of seedlings (obtained from a pool of upto 100 or more seeds) belonging to the CMS stock. One of the primers for detecting the polymorphic marker is labeled at the 5' end with a fluorescent tag such as flourescein, rhodamine and such other dyes that can be detected following PCR and electrophoresis using instruments like the Gene Scan facility of an ABI 377 DNA Sequencer or such other similar instruments known to those familiar with the art. By this assay, the extent of cross pollination can be detected by measuring the height of each of the peaks (each peak is characteristic of one allele) as detected by the instrument. If only one peak (corresponding to one allele) is detected, the sample of CMS seeds can be construed to be 100% pure. Impurities are detected by the occurrence of multiple alleles (peaks) in the sample. The ratio of the height of the contaminating peak (allele that is contributed to the population by the rogue donor) to the height of the expected peak (allele that is characteristic of the CMS line) will indicate the frequency of seeds within the CMS stock that have arisen following cross pollination with rogue pollen donors.

Although the application, as indicated above, is for estimating the extent of out-crossing that has occurred during the multiplication of CMS lines of rice, a similar approach can be used for estimating the extent of out-crossing that has occurred within the CMS lines of other crops including but not limited to maize, pearl millet, sorghum, wheat, sunflower, mustard, cabbage, cauliflower, tomato, pepper, okra, etc wherein the CMS lines are used for the production of hybrids and appropriate micro-satellite or STS markers are available.

The estimation of seed purity is an important quality control component of a hybrid rice program. This is conventionally done by the grow out test (GOT), which is based on the assessment of morphological and floral characteristics in plants grown to maturity (Ref). For the seed industry, large amounts of capital are locked up for extended periods in the form of stored hybrid seeds awaiting the results of the GOT. With the objective of replacing the GOT with DNA based assays, rice Cytoplasmic Male Sterile (CMS), Restorer and hybrid lines were screened to distinguish these, using microsatellite and Sequence Tagged Site (STS) polymorphisms. These co-dominant polymorphisms were identified after PCR, agarose gel electrophoresis and ethidium bromide staining. The principle of this method is that the hybrid would be heterozygous (i.e. both parental alleles would be present in the hybrid) when the genotype is assessed using microsatellite or STS markers that are polymorphic between the parental lines (i.e detect a different allele in the two parents). A simple procedure for DNA isolation and detecting heterozygosity and purity, has been standardised (described below) using three-day-old rice seedlings, and has been used for detection of impurities in hybrid seed lots (Example 10). Although multiple polymorphic markers can be used (either singly or by multiplexing) for assessing seed purity, for reasons of cost considerations, it is suggested that a single appropriately chosen microsatellite marker should be sufficient for assessing hybrid seed purity.

A variation of this assay is also described in Example 10 wherein the DNA is isolated from leaves obtained from a population of 400 seedlings (obtained from a pool of 400 seeds) belonging to the hybrid seed stock. One of the primers for detecting the polymorphic marker is labeled at the 5' end with a fluorescent tag such as flourescein, rhodamine and such other dyes that can be detected following PCR and electrophoresis using instruments like the Gene Scan facility of an ABI 377 DNA Sequencer or such other instruments known to those familiar with the art. By this assay, the extent of purity can be detected by measuring the height of each of the expected two peaks that are characteristic of the hybrid (each peak represents one allele that is contributed by one parent) that are detected by the instrument. Using genomic DNA isolated from a single hybrid plant as a template in the PCR assay, it is expected that the peak heights would be equal, leading to a ratio of 1:1 (or 50:50). Using genomic DNA isolated from a population of four hundred seedlings as a template in the PCR assay, any deviation from a ratio of 1:1 (50:50) for the heights of the two peaks would be an indicator of the extent of impurities in the hybrid seed stock. For eg., a ratio of peak heights of 1.02:0.98 (51:49) would correspond to a sample of hybrid seed stock that is 98% pure and a ratio of peak heights of 1.1:0.9 (55:45) would correspond to a sample of hybrid seed stock that is 90% pure.

The markers that are used for assessing hybrid seed purity should be carefully selected after taking into consideration, the varieties grown in adjacent fields that can serve as potential pollen donors either during CMS line multiplication (wherein only the Maintainer line should be the pollen donor) or hybrid seed production (wherein only the Restorer line should be the pollen donor). If pollination is by rogue pollen donors (i.e. lines that are neither Maintainers nor Restorers is found to occur), and the rogue donor is polymorphic with the CMS line in respect to the chosen microsatellite or STS marker, then heterozygosity would be observed even in the absence of production of the desired hybrid. Therefore, it is very important that the marker/s selected for assessing hybrid seed purity should be monomorphic between the CMS line and potential rogue pollen donors but polymorphic between CMS and Restorer lines. Detection of the expected heterozygosity will then be an indicator of hybrid seed production. These specific markers can be identified in polymorphism surveys conducted using either micro-satellite or STS markers on CMS, Restorer and potential rogue donor lines. Detection of these polymorphic markers would not be difficult for those familiar with prior art as a very large number of micro-satellite markers are currently available for rice (Temnykh et al, 2000).

The DNA marker assay is superior to the GOT in terms of speed and accuracy and it's implementation will result in considerable savings for the seed industry. Although the method was standardized for establishing the purity of rice hybrids produced through a three line breeding system of the type described in FIG. 1, it can also be applied for establishing the purity of rice hybrids obtained through a two line breeding system. In this two line breeding system, a conditionally male sterile line is used as the female parent for hybrid production by growing under conditions which induce male sterility. This line can be propagated by self fertilization when it is grown under conditions that do not induce male sterility. Therefore the need for Cytoplasmic Male Sterile and Maintainer lines can be avoided. The two line breeding systems are, by and large, in the experimental stages (except to a small extent in China). However, even for a two line system of hybrid seed production, the scheme for estimating hybrid seed purity would be the same as described for the three line breeding system. In this case, microsatellite and STS polymorphisms that distinguish the female and male parents (instead of the CMS and Restorer lines) would be identified and used as described above.

Although this method was standardised for establishing the purity of rice hybrids, it can also be used for establishing the purity of hybrids (produced either through the two line or three line breeding systems) in any other crop including but not limited to maize, pearl millet, sorghum, wheat, sunflower, mustard, cabbage, cauliflower, tomato, pepper, okra, etc for which suitable microsatellite and STS markers are available. It is anticipated that this assay (or variations thereof that would be apparent to those familiar with prior art) would find wide applications in hybrid seed quality control programs and result in significant benefits for the hybrid seed industry. The farmers who use seeds tested by this process would also benefit as they would be getting a properly authenticated product.

EXAMPLE 1

Isolation of genomic DNA from CMS and maintainer lines of rice.

Rice genomic DNA was isolated using either the protocols described by (a) Kochert et al. (1989) Rockefeller Program on Rice Biotechnology, Cornell Univ., New York, USA, or (b) Chunwongse et al (1993) Theor. Appl. Genet. 86:694–698, with slight modifications.

(a) Briefly, isolation using the Kochert et al protocol is as follows: 5–10 g of leaves obtained from 20 days old greenhouse grown plants were ground in a mortar and pestle in Liquid Nitrogen until a fine powder formed, without allowing powder to thaw. Sample were then transferred to chloroform-resistant 50 ml tubes (Polypropanol tubes) containing 25 ml of extraction buffer (420 g urea, 70 ml 5 M Nacl, 50 ml 1 M Tris-Hcl $_p$H 8.0, 80 ml 0.25 M EDTA, 200 ml 10% SDS, 50 ml Phenol reagent, volume made up to 1 litre with steriled double distilled water) pre-warmed to 60° C. Any clumps that formed were broken up with a glass rod and 0.750 ml of 20% Sodium Lauryl Sulfate was added and mixed well. The mixture was incubated at 60° C. for 10 minutes with inverting at regular intervals. This was cooled to room temperature and 15 ml of Chloroform:Isoamyl alcohol (24:1) was added and mixed well to get an emulsion. The tubes were centrifuged to separate the aqueous and chloroform phases. With a pipet, the aqueous upper phase was transferred into a fresh 50 ml tube. ⅔ to one volume of isopropanol was added to the final aqueous phase and inverted and mixed until DNA comes together. DNA was spooled out and transferred to a fresh tube containing 70% ethanol. DNA was pelleted by centrifugation and dried in a vacuum dryer after decanting the ethanol. DNA was dissolved in TE (Tris-Hcl 10 mM $_p$H 8.0 and EDTA 1 mM $_p$H 8.0).

(b) DNA isolation using the protocol of Chunwongse et al (1993) is as follows: seeds were germinated at 28° C. in the dark on moistened filter paper in Petri dishes. Three day old seedlings were crushed individually with a pestle in a 1.5 ml tube containing 200 μl of extraction buffer made up of 5% WN Chelex-100 (Bio-Rad Laboratories, USA) in sterile distilled water. The homogenate was incubated at 95° C. for 10 min and centrifuged at 12,000 rpm for 1 min. 10–15 μl of the supernatant was used for each PCR reaction.

EXAMPLE 2

Isolation of mitochondrial DNA from CMS and maintainer lines of rice.

Mitochondrial DNA was isolated from CMS and maintainer lines according to the protocols of Saleh et al. (1989) Theor. Appl. Genet. 77: 617–619. Surface sterilized seeds were germinated and grown for 14 days in a Greenhouse. The plants were then kept in the dark for three days for the plants to etiolate. After this step, all experiments were performed at 4° C. 20 g of leaves from 14 day old plants were collected and cut into small pieces. The leaves were homogenized in a mortar and pestle in 100 ml of Buffer A (10 mM TES $_p$H 7.2, 0.5 M Mannitol, 0.2% BSA, 0.05% cysteine). The homogenate was filtered through 4 layers of cheesecloth. This was Centrifuged at 5,000 rpm for 10 min and the supernatant was collected. The pellet was gently resuspended in 30 ml of Buffer A and centrifuged again at 5,000 rpm for 10 min. The supernatants were combined and centrifuged at 12,000 rpm for 10 min and the pellet was collected. The supernatant was centrifuged again at 12,000 rpm for 10 min and the two pellets were combined. The pellet was resuspended in Buffer A and centrifuged at 5,000 rpm for 10 min and the supernatant was collected. 1 M MgCl$_2$ and 10 mg/ml freshly prepared DNase I (in 0.15 M NaCl and 50% glycerol) was added to give a final concentration of 10 mM MgCl$_2$ and 10 μg DNase/g fresh weight of leaf tissue and incubated at 4° C. for 1 h. A sucrose gradient was made with Buffer B (10 mM TES $_p$H 7.2, 20 mM EDTA, 0.6 M sucrose) and 2 ml of mitochondrial suspension was loaded in each tube. This was centrifuged at 16,000 rpm for 10 min. The pellet was resuspended in 4 ml Buffer C (50 mM Tris-Hcl $_p$H 8.0, 10 mM EDTA $_p$H 8.0, 2% sarkosyl, 100 μg/ml proteinase K) and incubated at 37° C. on a shaker bath (Jolabo, Germany) with gentle agitation for 2 h. The lysate was made up to 0.2 M Ammonium acetate and purified by 3 cycles of phenol-chloroform extraction. Precipitation with 95% ethanol and subsequent washings were with 70% ethanol. The pellet was dried under vacuum. DNA was dissolved in TE, treated with Rnase A and stored at −20° C.

EXAMPLE 3

Identification of a DNA sequence that is specific to CMS lines of rice.

Primers used: Oligonucleotide primers for the RM9 microsatellite locus of rice (McCouch et al., 1996. Rice Genetics III, Proc. Third Intl. Rice Genet. Symp. Los Banos Manila, the Philippines. Oct. 16–20, 1995. International Rice Research Institute, Manila, the Philippines).

Forward: 5'-CAAAAACAGAGCAGATGAC-3' (SEQ ID No. 6)

Reverse: 5'-CTCMGATGGACGCCMGA-3' (SEQ ID No. 7)

Primers were synthesized by Oswel DNA Service, Southamton, U. K. Polymerase Chain Reaction (PCR) conditions were as described by McCouch et al. (1996) Rice Genetics III, Proc. Third Intl. Rice Genet. Symp. Los Banos Manila, the Philippines. Oct. 16–20, 1995. International Rice Research Institute, Manila, the Philippines with slight modifications. Briefly, PCR was performed in 25 μl reaction volume containing 50 to 100 ng of template DNA, 5 picomoles of each primer, 200 μM (each) deoxyribonucleotides, 50 mM KCl, 10 mM Tris-HCl, $_p$H 8.3, 1.5 mM MgCl$_2$, 0.01% gelatin and 1 unit of Taq polymerase. PCR conditions were: 95° C. for 7 min (initial denaturation), followed by 35 cycles of denaturation at 94° C. for 1 min, annealing at 55° C. for 1 min, extension at 72° C. for 2 min and a final extension of 5 min at 72° C. Samples were stored at 4° C. until further use. PCR products were detected by separating the DNA out in a 1% or 2% agarose gel by electrophoresis and staining with ethidium bromide to visualize the DNA fragments under Ultraviolet light.

PCR was performed using a Maintainer line, CMS line and the cognate hybrid. Apart from the expected DNA fragment amplified by the RM9 primer, an extra band was observed only in the CMS line and the hybrid but absent in the Maintainer line (FIG. 2).

EXAMPLE 4

Determination of a nucleotide sequence that is specific to CMS lines of rice.

Using RM9 primers, PCR was performed in 25 μl reaction volume containing 50 to 100 ng of template DNA, 5 picomoles of each primer, 200 μM (each) deoxyribonucleotides, 50 mM KCl, 10 mM Tris-HCl, pH 8.3, 1.5 mM MgCl$_2$, 0.01% gelatin and 1 unit of Taq polymerase. PCR conditions were: 95° C. for 7 min (initial denaturation), followed by 35 cycles of denaturation at 94° C. for 1 min, annealing at 55° C. for 1 min, extension at 72° C. for 2 min and a final extension of 5 min at 72° C. Samples were stored at 4° C. until further use. Amplified PCR products were separated on an agarose gel, stained with ethidium bromide and visualized under UltraViolet light. A DNA sequence of about 350 base pairs that is specific to CMS lines (FIG. 2) was than eluted out from the gel and purified using a Qiaquick Gel Extraction Kit (Qiagen, Germany) according to the Manufacturers' instructions. The purified DNA was than sequenced using an automated DNA sequencer ABI 3700 (ABI, Foster City, USA). The sequence obtained is shown in FIG. 3. A search for DNA homology in the GenBank indicates (FIG. 4) that most of the sequence has homology to a region of the rice mitochondrial DNA (DBJ Accession # D21251). However, a small part of the sequence did not exhibit any homology to rice mitochondrial DNA.

EXAMPLE 5

Design of specific oligonucleotide primers that can be used in a PCR assay to distinguish CMS and Maintainer lines of rice.

PCR primers were designed based on the sequence information obtained using the protocols described in Example 4. One primer was based on the part of the sequence that is unique to the CMS lines (base positions 1 to 36 in FIG. 3) and the other primer was based on the rice mitochondrial DNA sequence. The primers are:

Forward: 5'-ACTTTTTGTTTTTGTGTAGG-3' (SEQ ID No. 4)

Reverse: 5'-TGCCATATGTCGCTTAGACTTTAC-3' (SEQ ID No. 5)

EXAMPLE 6

A PCR assay for distinguishing CMS and Mantainer lines of rice.

Using the primer pair described in Example 5, PCR was performed in 25 μl reaction volumes with CMS and Maintainer lines as template DNA. The reaction composition was, 50–100 ng of template DNA, 1X PCR buffer (50 mM KCl, 10 mM Tris-HCl, pH 8.3, 1.5 mM MgCl$_2$, 0.01% gelatin), 200 μM dNTP (each), 1 unit of Taq polymerase and 5 pico moles of each primer. The PCR conditions were: Initial denaturation at 95° C. for 7 min followed by 35 cycles of 94° C. for 30 sec, 44° C. for 1 min, 72° C. for 2 min. A final extension was given at 72° C. for 7 min and then the samples were stored at 4° C. until further use. PCR products were separated on a 1% agarose gel and the DNA bands detected by staining with ethidium bromide and visualizing under ultraviolet light. Using this primer pair, there was an amplification of a 350 bp DNA fragment in the CMS lines but no PCR amplification was observed in the Maintainer lines (FIG. 5).

EXAMPLE 7

A DNA-DNA hybridisation assay using CMS specific PCR amplified DNA fragment as a probe for detection of Restriction Fragment Length Polymorphisms (RFLP) that distinguish the CMS and Maintainer lines.

Genomic DNA isolated (as described in Example 1 (a) from IR 58025 A (CMS) and IR 58025 B (Maintainer) lines of rice were digested with various restriction enzymes viz. EcoR I, Hind III, Dra I, EcoR V, Hinc II, Sau 96 I, Taq αI (New England Biolabs Inc., MA, USA). Three to four micrograms of completely digested DNA from both CMS and Maintainer lines were separated electrophoretically on 0.7% agarose (Sigma, USA) gels, denatured, neutralized, and vacuum transferred to Hybond N (Amersham Life Science, Buckinghamshire, England) membranes according to the procedure given by Sambrook et al (1989) Cold Spring Harbor, N.Y., USA. DNA was crosslinked to membrane using a UV Stratalinker (Stratagene, La Jolla, Calif., USA). Blots were pre-hybridized in a solution of 0.5 M sodium phosphate (pH 7.2), 7% Sodium dodecyl sulfate (SDS), 1% bovine serum albumin and 1 mM EDTA for 3 h at 65° C. Probe (PCR amplification product of SEQ ID No. 4 and SEQ ID No. 5) was labeled with α$^{32}$P-dATP using a random primer labelling kit (JONAKI-BRIT, Mumbai, India) as described by the manufacturer and hybridized for 18 h at 65° C. with constant shaking. Blots were washed at 65°C. with 2×SSC (1×SSC=0.15 M sodium chloride, 0.015 M sodium citrate, pH 7.0), 0.1% SDS and 5 mM sodium phosphate (pH 7.0) for 3×20 min and with 0.5×SSC, 0.1% SDS and 3 mM sodium phosphate buffer (pH 7.0) for 3×20 min. Autoradiography was done by exposing the blots to X-Ray film at −70° C. As an illustration, the RFLP obtained using the restriction enzyme EcoR V is depicted in FIG. 6.

EXAMPLE 8

A multiplex PCR assay for distinguishing CMS and Maintainer lines of rice.

We have also developed a multiplex PCR assay wherein a first set of oligonucleotide primer (Table 2 shown at the end of the description) can be successfully multiplexed in a single PCR with any primer pair belonging to a second set of oligonucleotide primers (Table 3) to distinguish CMS and Maintainer lines.

The first set of primers amplify a 325 bp fragment using template DNA from CMS line as a target but no amplification product is obtained using genomic DNA of the Maintainer line as a target. Any primer pair belonging to the second set of oligonucleotide primers will amplify a single fragment irrespective of whether the target DNA is from either the CMS or the Maintainer line. This procedure is described below. Rice genome sequences available in the public domain (GeneBank) were downloaded and primers were designed based on these sequences. One primer pair was based on the sequence of rice chromosome I (Accession #AP001859; between positions 1372 and 2598 of the sequence in the database) and the oligonucleotide sequences are:

Forward 5'-AACACAAGGGACAGCACATTGAGC-3' (SEQ ID No. 8)

Reverse 5'-GAAAGAGGAGCTAGAGGTGGGTGC-3' (SEQ ID No. 9)

This primer pair gives a PCR amplification product of 1.1 kb.

Two other primer pairs were designed based on the sequence of the rice mitochondrial DNA (Accession #D21251) between positions 4981 and 5641 of the sequence for SEQ ID No. 10 and SEQ ID No. 11 and between positions 6660 and 7303 of the sequence for SEQ ID No. 12 and SEQ ID No. 13 in the database:

(1)

Forward 5'-GGGCAATTCCATCGTGCTATGAGC-3' (SEQ ID No. 10)

Reverse 5'-GCGTTGGGTTTTCCAACGAAAAAC-3' (SEQ ID No. 11)

This primer pair gives a PCR amplification product of 660 bp.

(2)

Forward 5'-CAGGCAAGGTCATAATTCGCAGG-3' (SEQ ID No. 12)

Reverse 5'-CGAAGAAGCAGTCTTGCTTCCTC-3' (SEQ ID No. 13)

This primer pair gives a PCR amplification product of 600 bp.

Each of these three primer pairs was individually multiplexed in a PCR in combination with the Oligonucleotide primer pair indicated in Table 2 (SEQ ID No. 4 and SEQ ID No. 5) using the following conditions: 50–100 ng of template DNA, 1×PCR buffer (50 mM KCl, 10 mM Tris-HCl, $_p$H 8.3, 1.5 mM MgCl$_2$, 0.01% gelatin), 200 µM dNTP (each), 1 unit of Taq polymerase, 5 pico moles each of primers from Table 2 (Seq ID No. 4 and SEQ ID No. 5) and 1 pico mole each of any of the primer pairs from Table 3. The PCR conditions were: Initial denaturation at 95° C. for 7 min followed by 35 cycles of 94° C. for 30 sec, 44° C. for 1 min, 72° C. for 2 min. A final extension was given at 72° C. for 7 min and then the samples were stored at 4° C. until further use. PCR products were separated on a 1% agarose gel and the DNA bands detected by staining with ethidium bromide and visualizing under ultraviolet light. As depicted in FIG. 7, the 325 bp fragment amplified by primers SEQ ID No. 4 and SEQ ID No. 5 is obtained only when the template DNA is from the CMS line. Each of the primer pairs in Table 3 (SEQ ID No. 8 and 9, SEQ ID No. 10 and 11, SEQ ID No. 12 and 13) amplified a specific DNA fragment irrespective of whether the template DNA is from the CMS line or the Maintainer line. Therefore, in this multiplex PCR assay, two DNA fragments are observed when the template is from the CMS line and only a single DNA fragment is obtained if the template DNA is from the Maintainer line. In FIG. 7 (Lane 2 and 3), an example of a PCR performed with a single primer pair (SEQ ID No. 4 and 5) that is specific for CMS line and a multiplexed PCR performed with primers SEQ ID No. 4 and 5, and SEQ ID No. 8 and 9 (Lane 4 and 5) is shown.

EXAMPLE 9

A PCR assay for detecting impurities within CMS lines that have arisen due to cross pollination with rogue pollen donors.

Genomic DNA is isolated as described in Example 1 (b) from 100 three day old seedlings obtained by germination of seeds of the CMS stock. PCR as described in Example 7 (with variation in cycling conditions as per the source of the primers) is performed by using oligonucleotide primers that target any one of a number of microsatellite markers that will detect polymorphism between the CMS line and the rogue pollen donor. After PCR, the product is separated on an agarose gel and detected by ethidium bromide staining. A single band will be observed if DNA is from the CMS line but if cross pollination has occurred from a rogue pollen donor, an extra band (contibuted by the rogue pollen donor) will be observed apart from the CMS specific band.

A PCR assay for detecting impurities within CMS lines that have arisen due to cross pollination with rogue pollen donors can also be performed on DNA isolated from a pool of 100 seedlings obtained by germination of the seeds of the CMS stock. Grow 100 CMS rice seedlings up to 15 days and from each plant, remove two cm from the tip of the second leaf and then cut a one cm long leaf piece below this area. Pool the cut leaves from all the plants and isolate genomic DNA as described in Example 1 according to the protocol of Kochert et al (1989). Label 5' end of one of the primers (either forward or reverse) with fluorescent dye using standard protocols. Do PCR reactions with the Fluorescent labeled primers, generally as described in Example 7. The cycling conditions can vary according to the primer in use. Important to note, the template DNA used should be only 2–3 ng and AmpliTaq Gold (ABI, Foster City, USA) enzyme should be used. After PCR, take 1 µl of PCR product and mix with loading dye (Formamide and Blue dextron 5:1 ratio) and 1.5 µl marker (ABI, Foster City, USA). Heat denature and load 1.5 µl of the sample in an automated DNA sequencer 377 (ABI, Foster City, USA). Run the gel till the bands are separated properly. Analyse the peak heights produced by the bands using the GeneScan analyser (ABI, Foster City, USA).

EXAMPLE 10

A PCR assay for detecting purity of rice hybrids.

Genomic DNA from CMS line IR 58025 A, Restorer IR40750 and the hybrid (DRR H1) of these two parents, were isolated as described in Example 1 (b). PCR was performed using the microsatellite marker RM164 [Forward 5'-TCTTGCCCGTCACTGCAGATATCC-3' (SEQ ID No. 14), Reverse 5'-GCAGCCCTAATGCTACAATTCTTC-3' (SEQ ID No. 15)] (Wu and Tanksley, 1993. Mol. Gen. Genet. 241:225–235). A polymorphism between the two parents is observed at this locus. The PCR conditions were: DNA samples (50 ng) were amplified in 25 ml reaction volumes containing 1×PCR buffer [10 mM Tris.HCl (pH 8.3), 50 mM KCl, 1.5 mM MgCl$_2$, 0.01% gelatin], 0.2 mM of each dNTPs (Amersham Pharmacia Biotech, Sweden), 10 Pico moles of each primer and 1U of Taq polymerase. Initial denaturation at 95° C. for 7 min followed by 35 cycles of 94° C. for 1 min, 55° C. for 1 min, 72° C. for 2 min. A final extension was given at 72° C. for 7 min and then the samples were stored at 4° C. until further use. The PCR product was separated on an agarose gel, stained with ethidium bromide and visualized under ultraviolet light. The result of the PCR performed using the SEQ ID No. 14 and SEQ ID No. 15 as primers is shown in FIG. 8. True hybrids exhibited two DNA fragments, one fragment contributed by the Restorer parent and the other fragment contributed by the CMS parent. The off-types exhibits a single fragment which co-migrates with the DNA band of either of the parents (FIG. 8). In FIG. 8, the off-type co-migrates with the CMS DNA band which suggest that this particular hybrid seed lot is contaminated with the Maintainer line of IR 58025 A (CMS). The microsatellite marker used in this experiment is shown only as an example of the hundreds of microsatellite markers that can be used for detecting hybrid seed purity in rice.

A PCR method that can detect purity of rice hybrids can also be done in pooled samples. Grow 400 rice seedlings obtained by germination of seeds belonging to the hybrid seed stock for up to 15 days and from each plant, remove 2 cm from the tip of the second leaf and then cut 1 cm leaf piece below this area. Pool the cut leaves from all the plants and isolate genomic DNA as described in Example 1 according to the protocol of Kochert et al (1989). Label 5' end of one of the primers (either forward or reverse) with fluorescent dye using standard protocols. Do PCR reactions with the Fluorescent labeled primers, generally as described in Example 7. The cycling conditions can vary according to the primer in use. Important to note, the template DNA used should be only 2–3 ng and AmpliTaq Gold (ABI, Foster City, USA) enzyme should be used. After PCR, take 1 µl of PCR product and mix with loading dye (Formamide and Blue dextron 5:1 ratio) and 1.5 µl marker (ABI, Foster City, USA). Heat denature and load 1.5 µl in an automated DNA sequencer 377 (ABI, Foster City, USA). Run the gel till the bands are separated properly. Analyse the peak heights produced by the bands using the GeneScan analyser (ABI, Foster City, USA).

By this assay, the extent of purity can be detected by measuring the height of each of the expected two peaks that are characteristic of the hybrid (each peak represents one allele that is contributed by one parent) that are detected by the instrument. Using genomic DNA isolated from a single hybrid plant as a template in the PCR assay, it is expected that the peak heights would be equal, leading to a ratio of 1:1 (or 50:50). Using genomic DNA isolated from a population of four hundred seedlings as a template in the PCR assay, any deviation from a ratio of 1:1 (50:50) for the heights of the two peaks would be an indicator of the extent of impurities in the hybrid seed stock. For eg., a ratio of peak heights of 1.02:0.98 (51:49) would correspond to a sample of hybrid seed stock that is 98% pure and a ratio of peak heights of 1.1:0.9 (55:45) would correspond to a sample of hybrid seed stock that is 90% pure.

In conclusion, it can be said that the invention provides a method for ensuring the purity of parental lines is an essential prerequisite for ensuring the purity of rice hybrids. The cytoplasmic male sterile lines that are used in the three line breeding system for hybrid rice production are often contaminated with seeds of the iso-nuclear maintainer lines. Herein is reported a DNA Sequence that is homologous to rice mitochondrial DNA but is unique to the WA cytoplasmic male sterile lines of rice. In a Polymerase Chain Reaction (PCR) using total genomic DNA as a template, oligonucleotide primers based on this said DNA sequence PCR amplify a fragment from cytoplasmic male sterile lines of rice but not from their cognate maintainer lines indicating that this PCR assay can be used to detect impurities of the maintainer lines within seed stocks of the CMS line. In a coded test on a mixed sample of plants containing both CMS and maintainer lines, this PCR assay was used to correctly predict the genotypes of these plants. In Southern hybridization analysis, the PCR amplified fragment obtained using these oligonucleotide primers detect a polymorphism between the CMS and maintainer lines. Also described is the application of co-dominant PCR assayable markers like Microsatellites and Sequence Tagged Site polymorphisms for detecting contaminating cross pollination during CMS line multiplication as well as for assessing the purity of rice hybrids is described.

TABLE 1

Rice lines analysed in this study*

CMS lines

IR 58025 A
IR 62829 A
PMS 8 A
PMS 10 A
78897 A

Maintainer lines

IR58025 B
IR 62829 B
PMS 8 B
PMS 10 B
78897 B

Restorer line

IR40750

Hybrid

DRRH 1 (IR 58025 A × IR 40750)

*All rice lines used in this study were provided by the Directorate of Rice Research, Indian Council of Agricultural Research, Hyderabad, India.

TABLE 2

Sequence specific oligonucleotide primers for a PCR assay to distinguish CMS and Maintainer lines of rice.

| Oligonucleotide primer pair | Locus being amplified | Size of amplified fragment | Polymorphism between CMS lines & Maintainer |
|---|---|---|---|
| (1) F 5'-ACTTTTTGTTTTGTGTAGG-3' (SEQ ID No. 4) R 5'-TGCCATATGTCGCTTAGACTTTAC-3' (SEQ ID No. 5) | Rice mitochondrial DNA (a genomic region encoding genes for ribosomal protein S3, L16, S12 and NADH dehydrogenase subunit 3) | 325 bp | Yes |

TABLE 3

Sequences of oligonucleotide primers that can be multiplexed with SEQ ID No. 4 and SEQ ID No. 5 in a PCR assay for the differentiation of CMS and Maintainer lines.

| Oligonucleotide primer pair | Locus being amplified | Approximate size of amplified fragment | Polymorphism between CMS & Maintainer lines |
|---|---|---|---|
| (1) F 5'-AACACAAGGGACAGCACATTGAGC-3' (SEQ ID No.8) R 5'-GAAAGAGGAGCTAGAGGTGGGTGC-3' (SEQ ID No.9) | Rice Chromosome I (positions 1372 to 2598 of Accession #AP001859) | 1178 bp | No |
| (2) F 5'-GGGCAATTCCATCGTGCTATGAGC-3' (SEQ ID No. 10) R 5'-GCGTTGGGTTTTCCAACGAAAAAC-3' (SEQ ID No. 11) | Rice mitochondrial DNA (positions 4981 to 5641 of Accession #D21251) | 660 bp | No |

TABLE 3-continued

Sequences of oligonucleotide primers that can be multiplexed with SEQ ID No. 4 and SEQ ID No. 5 in a PCR assay for the differentiation of CMS and Maintainer lines.

| Oligonucleotide primer pair | Locus being amplified | Approximate size of amplified fragment | Polymorphism between CMS & Maintainer lines |
|---|---|---|---|
| (3) F 5'-CAGGCGAAGGTCATAATTCGCAGG-3' (SEQ ID No. 12)<br>R 5'-CGAAGAAGGCAGTCTTGCTTCCTC-3' (SEQ ID No. 13) | Rice mitochondrial DNA (positions 6660 to 7303 of Accession #D21251) | 643 bp | No |

F = Forward primer, R = Reverse primer

---

What is claimed is:

1. An isolated DNA sequence consisting of SEQ ID NO: 1 or SEQ ID NO: 3.

2. A pair of oligonucleotide primers, said pair comprising a first primer comprising SEQ ID No: 4 and a second primer comprising SEQ ID No: 5.

3. A method of distinguishing Male Sterile (CMS) lines of rice from their cognate Male Fertile Maintainer Lines comprising the steps of:
   (a) providing a pair of oligonucleotide primers, said pair comprising a first primer comprising SEQ ID No: 4 and a second primer comprising SEQ ID No: 5;
   (b) conducting a Polymerase Chain Reaction (PCR) assay on a rice sample using the oligonucleotide primer pair; and
   (c) detecting PCR-amplified fragment(s);
wherein the presence of PCR-amplified fragments indicates the sample is from a CMS line, and the absence of PCR-amplified fragments indicates the sample is from the cognate Male Fertile Maintainer line.

4. The method of claim 3, wherein said Male Sterile Lines contain the WA (wild abortive) cytoplasm.

5. The method of claim 3, wherein detecting PCR-amplified fragment(s) comprises conducting agarose gel electrophoresis followed by Ethidium bromide staining.

6. The method of claim 3, wherein detecting PCR amplified fragment(s) comprises incorporating at least one radioactively labeled nucleotide into the PCR amplified fragment(s) and detecting the radioactively labeled nucleotide(s).

7. The method of claim 3 wherein detecting PCR amplified fragment(s) comprises incorporating at least one non-radioactively labeled nucleotide into the PCR amplified fragment(s) and detecting the non-radioactively labeled nucleotide by colorimetry, chemiluminescence or measurement of fluorescence.

8. A method of distinguishing WA Cytoplasmic Male Sterile lines of rice from their cognate Male Fertile Maintainer lines, comprising the steps of:
   (a) providing a pair of oligonucleotide primers, said pair comprising a first primer comprising SEQ ID No: 4 and a second primer comprising SEQ ID No: 5;
   (b) conducting a PCR-Enzyme Linked Immunosorbent Assay (PCR-ELISA) on a rice sample using the oligonucleotide primer pair; and
   (c) detecting PCR-amplified fragment(s);
wherein the presence of PCR-amplified fragments indicates the sample is from a WA Cytoplasmic Male Sterile line, and the absence of PCR-amplified fragments indicates the sample is from the cognate Male Fertile Maintainer line.

9. The method of claim 3 wherein detecting PCR amplified fragment(s) comprises using fluorescently labeled nucleotides in Fluorescence Resonance Energy Transfer (FRET).

10. A method of distinguishing Male Sterile (CMS) lines of rice from their cognate Male Fertile Maintainer Lines comprising:
    a) providing a first pair of oligonucleotide primers, said first pair comprising a first primer comprising SEQ ID No: 4 and a second primer comprising SEQ ID No: 5, and a second pair of oligonucleotide primers, wherein the second pair of oligonucleotide primers is derived from any sequenced portion of a rice genome outside a region targeted by the first primer pair;
    b) conducting a multiplex PCR assay on a rice sample using said first and second pairs of oligonucleotide primers; and
    c) detecting amplified target DNA sequences;
wherein a DNA amplification product is obtained using the first pair of primers only if the template DNA is obtained from the WA Cytoplasmic Male Sterile lines but not from the Male Fertile Maintainer Line; and another DNA amplification product is obtained using the second pair of primers irrespective of whether the template DNA is form a CMS or a Male Fertile Maintainer Line; and
wherein successful amplification of the respective target DNA Sequences occurs when the two primer pairs are included in the same PCR mixture.

11. The method of claim 10 wherein several oligonucleotide primer pairs are multiplexed in a PCR assay with the first pair of oligonucleotide primers.

12. The method of claim 8, wherein the PCR-ELISA comprises one or more of: using a labeled capture probe or labeled PCR primer that can be bound to suitably coated solid surface made of polystyrene, styrene or glass; using a non-radioactively labeled nucleotides in the PCR and subsequently detecting with anti-label antibodies that are conjugated to enzymes used for ELISA; and modifying the PCR-ELISA format by using an alternate method for labeling the PCR amplified fragment, attaching probe to solid surfaces or detecting the PCR amplified fragment.

* * * * *

SEQUENCE LISTING

<160> NUMBER OF SEQ ID NOS: 15

<210> SEQ ID NO 1
<211> LENGTH: 323
<212> TYPE: DNA
<213> ORGANISM: Artificial Sequence
<220> FEATURE:
<223> OTHER INFORMATION: Description of Artificial Sequence: Nucleotide
      sequence specific to CMS lines of rice

<400> SEQUENCE: 1

```
acggccctca tcaccttctt tcactttttg ttttttgtgta ggtgagtcaa ttgcgtgtgg      60
ccttcaagta tttcgtattg taacaatatt cgatcggcat ccaaacaaag gtgcatgtac     120
ggttcctaag ggatacaatt ttgtcttaaa tcatcgagaa agattaaggt aagttgatag     180
gcgcgatctc gtacctaaca catactctct aaatattgaa gaacttgcat gcggccttca     240
agccacaacg cggtatgagt tctttgtttg ggggctgctt gccccttcgc gtcgacaagg     300
aaactgagga cgacaatggc acc                                             323
```

<210> SEQ ID NO 2
<211> LENGTH: 350
<212> TYPE: DNA
<213> ORGANISM: Artificial Sequence
<220> FEATURE:
<223> OTHER INFORMATION: Description of Artificial Sequence: Sequence
      homologous to sequence of CMS rice lines

<400> SEQUENCE: 2

```
gagcacttcc ccagaggcag aggctgagtc tacaaaaggg cgggagcata aaatgtaggt      60
gagtcaattg cgtgtggcct tcaagtattt cgtattgtaa caatattcga tcggcatcca     120
aacaaaggtg catgtacggt tcctaaggga tacaattttg tcttaaatca tcgagaaaga     180
ttaaataagt tgatagcgcg atctcgtact aacacatact ctctaaatat tgaagaactt     240
gcatgcggcc ttcaagccac aaccgcggta tgagttcttt gtttggggggc tgcttgcccc     300 ttcgcgtcga caaggaaact gtggacgaca atgggtttag aattagaata               350
```

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Sequence
      absent in rice mitochondrial DNA

<400> SEQUENCE: 3

```
acggccctca tcaccttctt tcactttttg tttttg                                36
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: forward
      primer

<400> SEQUENCE: 4

```
acttttttgtt tttgtgtagg                                                 20
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: reverse
      primer

<400> SEQUENCE: 5

```
tgccatatgt cgcttagact ttac                                             24
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Forward
      primer

<400> SEQUENCE: 6

```
caaaaacaga gcagatgac                                                   19
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: reverse
      primer

<400> SEQUENCE: 7

```
ctcaagatgg acgccaaga                                                   19
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Forward
      primer

<400> SEQUENCE: 8

```
aacacaaggg acagcacatt gagc                                             24
```

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Reverse
      primer

<400> SEQUENCE: 9

```
gaaagaggag ctagaggtgg gtgc                                             24
```

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Forward
      primer

<400> SEQUENCE: 10
gggcaattcc atcgtgctat gagc                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Reverse
      primer

<400> SEQUENCE: 11
gcgttgggtt ttccaacgaa aaac                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Forward
      primer

<400> SEQUENCE: 12
caggcgaagg tcataattcg cagg                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Reverse
      primer

<400> SEQUENCE: 13
cgaagaaggc agtcttgctt cctc                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Forward
      primer

<400> SEQUENCE: 14
tcttgcccgt cactgcagat atcc                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Reverse
      primer

<400> SEQUENCE: 15
gcagccctaa tgctacaatt cttc                                              24
```